United States Patent [19]

Heimke et al.

[11] Patent Number: 4,959,054
[45] Date of Patent: Sep. 25, 1990

[54] PHARMACEUTICALLY PROTECTED PERCUTANEOUS DEVICES

[75] Inventors: Gunther Heimke, Clemson; Andreas F. von Recum, Six Mile; Arun Shanbhag, Spartanburg, all of S.C.

[73] Assignee: Clemson University, Clemson, S.C.

[21] Appl. No.: 276,156

[22] Filed: Nov. 23, 1988

[51] Int. Cl.⁵ .............................................. A61M 5/00
[52] U.S. Cl. ..................................... 604/175; 604/280; 604/93
[58] Field of Search ................... 604/53, 106, 265, 280, 604/175, 174, 265, 93

[56] References Cited

U.S. PATENT DOCUMENTS

| | | | |
|---|---|---|---|
| 3,447,161 | 6/1969 | Weikel | 604/289 |
| 4,578,063 | 3/1986 | Inman et al. | 604/175 |
| 4,676,782 | 6/1987 | Yamamoto et al. | |
| 4,810,246 | 3/1989 | Frisch et al. | 604/175 |

OTHER PUBLICATIONS

W. L. Gore & Associates, Inc., Peritoneal Catheter. Study Results of the Premarket VITACUFF Infection Control Device, publication date unknown.
Gross–Siestrup et al, "Design Criteria for Percutaneous Devices," Journal of Biomedical Materials Research, vol. 18, pp. 357–382 (1982).

Primary Examiner—C. Fred Rosenbaum
Assistant Examiner—Denise W. DeFranco
Attorney, Agent, or Firm—Dority & Manning

[57] ABSTRACT

A percutaneous implant device includes a structure for storing a bioreactive agent such as an antimicrobic agent, an anti-inflammatory drug, a growth hormone, and an antifungal drug. The structure can take the form of a container or a solid solution. The percutaneous device has a conduit, and the structure containing the bioreactive agent is disposed under the skin and around the conduit in the vicinity where the conduit passes through the skin of the living host. The structure containing the bioreactive agent is refillable via either a wall which is penetrable and reseals after penetration, or an access opening which can be opened or closed and is accessible from outside the living host. The container can include a wall having a diffusion coefficient which increases the rate of diffusion with increasing local temperature.

20 Claims, 6 Drawing Sheets

PHARMACEUTICALLY PROTECTED PERCUTANEOUS DEVICES

BACKGROUND OF THE INVENTION

The present invention relates to percutaneous implant devices and in particular to pharmaceutically protected percutaneous implant devices.

A percutaneous device functions to maintain an opening in the skin through which either wires or pipes can pass from the outside world into the bodies of men or animals. Thus, percutaneous devices serve as lead throughs for either wires or pipes from the outside world into the bodies of men or animals.

The outside surface of a wire or pipe usually lacks compatibility with the living body tissues. Thus, a percutaneous device consists of a structure having an opening to receive the wire or pipe and an outside surface sufficiently compatible with the skin and the subcutaneous tissue to avoid rejection for a period of time useful to the patient. The percutaneous device interfaces with the body tissue and has an inner surface that provides a close, bacteria-tight junction with the outside surface of the wire or pipe that penetrates into the interior of the living body.

Movement of the percutaneous device causes irritation at the site where the device contacts the skin and the subcutaneous tissue. Such irritation contributes to early failure and rejection of the percutaneous implant. Thus, many percutaneous devices include a flange intended to be implanted subcutaneously to distribute mechanical forces over a larger area than the cross-section of the pipe or wire. This distribution of mechanical forces reduces the mechanical irritation that results at the junction of the living tissue and the percutaneous device.

When bacteria and other foreign bodies invade the junction between the skin and the implant, this too causes the failure or rejection of percutaneous devices.

Foreign material entering the junction where the gingival tissue surrounds a natural tooth can cause an inflammatory reaction. However, the gingival and subgingival region immediately adjacent to the surface of the tooth contain entities which stimulate an increased, localized, phagocyte activity as soon as any foreign material enters into the junction between the gingival tissue surrounding natural teeth and the tooth itself.

A solid solution of Gentamicin in methylmethacrylate has been used successfully in orthopaedic surgery, but has not found a use in connection with percutaneous implants prior to the present invention.

Polymethylmethacrylate, which is usually called bone cement or abbreviated PMMA, has been used to fix joint replacements, like artificial hip joints or knee joints, into the surrounding bony tissue adjacent to the joint. As the PMMA cures, it takes the antibiotic Gentamicin into solid solution. The temperature of PMMA reaches 100° C. during the curing, and most other antibiotics do not survive this curing process because their molecular structures are too complicated. The Gentamicin diffuses out of the cured PMMA over very long periods of time, on the order of years, so that a local concentration of this antibiotic can be maintained without subjecting the whole body to this concentration. Moreover, the local concentration is sufficient to ensure that the bacteria will be destroyed in the immediate environment of the PMMA. This technique is widely used in particular in secondary joint replacement operations where the danger of infection is much higher than in primary operations. In such cases, the Gentamicin containing cement remains in situ for the lifetime of the implant and hopefully for the whole lifetime of the patient.

Infected bone wounds and infection in bony tissue provide other applications for PMMA infused with Gentamicin. In these cases, the general practice is to prefabricate PMMA into small spheres, each having a little stainless steel wire extending diametrically through it. These wires are connected to each other to form a chain. Such chains are inserted into infected areas in bony tissue, left there until the infection has ceased, and then removed in a second operation. Thus, when the Gentamicin diffusing from the spheres has eliminated the infection, the surgeon can remove the spheres by getting hold of a single sphere and just pulling out the entire chain of spheres.

FIG. 28 of Grosse-Siestrup et al, "Design Criteria for Percutaneous Devices," Journal of Biomedical Materials Research, Volume 18, pp. 357–82 (1982), illustrates a device for periodically treating the three-phase junction between the percutaneous device, the skin, and the outside air. It comprises an annular sleeve which is slipped over the lead-through and placed above the skin and intended to float in the three-phase junction. This annular sleeve provides a conduit for liquids, such as cleaning fluids or antibiotics, which are pumped through the sleeve via a squeeze bulb or the like, to clean the outside part of the skin adjacent to the percutaneous device. The device is then removed until the procedure is repeated. However, these devices to date have failed to extend the time between implantation and failure of the percutaneous device to any significantly appreciable extent. They also require the periodic attention of a human operator.

An infection control device that is related to vascular catheters is known by the brand name VITA CUFF and distributed by Baxter Health Care Corporation of McGaw Park, Illinois. The VITA CUFF device also surrounds a cylindrical catheter at a desired anatomical site and secures itself to the catheter by applying radial compression to the catheter. The VITA CUFF device has an outer tissue-interfacing surface that has a porous matrix consisting of a collagen sponge. Silver ions are bound to the collagen matrix to provide antimicrobial activity during the four to six weeks it takes for the collagen sponge to be completely absorbed by the surrounding tissue. Thus, this device likewise fails to extend the useful life of the implant for a period on the order of several months or years.

OBJECTS AND SUMMARY OF THE INVENTION

It is the principal object of the present invention to provide a percutaneous device having a prolonged useful life relative to conventional percutaneous devices.

It is another object of the present invention to provide a percutaneous device that mimics the biochemistry of the gingival and subgingival tissue surrounding teeth in order to prolong the useful life of such percutaneous device relative to conventional percutaneous devices.

It is a yet further principal object of the present invention to provide a percutaneous device that provides means to pharmaceutically protect the interface between the skin and the device in order to significantly prolong the useful life of such percutaneous device relative to a conventional percutaneous device.

It is a still further object of the present invention to provide a percutaneous device having a receptacle for storing pharmaceutical and disposed to permit discharge of the pharmaceutical to the vicinity of the interface of the skin and the percutaneous device.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the percutaneous implant device of the present invention comprises a conduit for leading through the skin and subcutaneous tissue of a living human being or animal. As embodied herein, the conduit preferably is a tube or pipe formed of a bio-compatible material such as silicon, titanium, polycarbonate, etc. Preferably, only the tissue interfacing surface of the conduit need be formed of a bio-compatible material. Accordingly, various composite structures are suitable as conduits for purposes of the present invention.

The present invention further includes means for dispensing a bioactive agent during the useful life of the percutaneous device. The dispensing means is disposed on the portion of the conduit beneath the skin and preferably contacts the conduit in the vicinity of the opening through the skin and completely surrounds the conduit. Moveover, the dispensing means preferably is structured so as to maintain a predetermined size and so does not diminish while continuously dispensing the bioactive agent during the useful life of the percutaneous device. Since the dispensing means neither expands nor contracts, the formation of voids in the subcutaneous tissue is avoided.

In one preferred embodiment, the means for dispensing a bioactive agent includes a container having a hollowed receptacle for storing a bioactive agent. The container at least partly surrounds the conduit and preferably completely surrounds the conduit. The container preferably is disposed beneath the skin and in the subcutaneous tissue so as to permit the bioactive agent to be diffused in the vicinity of the interface between the conduit and the skin through which the conduit leads.

The container preferably is formed of one or more of the following materials: silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon. The container preferably includes a tissue interfacing wall which is permeable to the bioactive agent in order to permit the bioactive agent to be diffused through the wall and into the body tissue adjacent the wall. Moreover, the tissue interfacing wall preferably is formed of a material having a permeability co-efficient which is temperature dependent, and preferably this temperature dependence is such that the permeability of the wall increases as the temperature increases. Examples of materials suitable for forming the tissue interfacing wall include silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon. Such materials can be formed with varying porosities according to known techniques, and these porosities can be controlled to optimize them for a preselected bioactive agent and a desired diffusion rate.

In another preferred embodiment, the means for dispensing a bioactive agent during the active life of the percutaneous device includes a plurality of solid pieces for containing a bioactive agent in solid solution. The pieces have at least a surface portion thereof forming a free surface for interfacing with the tissue of the body in which the implant is embedded. For example, the pieces disposed in a flange have a tissue interfacing surface forming part of the surface of the flange which interfaces with the tissue surrounding the implant. The pieces can be formed of polymethylmethacrylate for example and used to hold a bioactive agent such as Gentamicin in solid solution to be dispensed by gradual diffusion over a period of many years into the tissue.

Suitable bioactive agents include antimicrobial agents, growth hormones, anti-inflammatory drugs, broad spectrum antibiotics, and antifungal agents, to name a few. Some specific examples of suitable bioactive agents include the following antimicrobial agents effective against Gram Positive Bacteria: Penicillin G, Methicillin, Nafcillin, Oxacillin, Rifampin, Vancomycin, Streptomycin, Cephalosporins, and Bacitracin. Some specific examples of suitable bioactive agents include the following antimicrobic agents effective against Gram Negative Bacteria: Neomycin, Polymyxins, and Vancomycin. Some specific examples of suitable bioactive agents include the following broad spectrum antimicrobic agents: Gentamicin, Ampicillin, Chloramphenicol, Kanamycin, Sulfa drugs, and Tetracycline. Some specific examples of bioactive agents in the anti-inflammatory drug category suited to the present invention are believed to include Cortisone and steroids. Some specific examples of suitable bioactive agents include the following antifungal agents: Amphotericin B, Clotrimazole, and Nystatin. Moreover, suitable bioactive agents can be formed by known effective combinations of any of the foregoing, which also can be provided in different solutions as desired. In addition, different bioactive agents can be alternated so as to alter the treatment required by the implant during different stages of its useful life.

One of the purposes behind the requirement that the size of the container or the pieces be maintained during dispensing of the bioactive agent is the avoidance of voids which might provide sites for the initiation of inflammation or infection. Another purpose is to facilitate location of a suitable site for refilling the container or the pieces with bioactive agent as described hereinafter in order to further prolong the useful life of the implant.

In an alternative preferred embodiment of the present invention, a flange surrounds the conduit. The flange extends radially outwardly from the conduit to a free edge. The stiffness of the flange preferably decreases gradually as an imaginary point starts from the portion of the flange contacting the conduit and moves in the direction toward a free edge of the flange. The decreasing stiffness can be accomplished by decreasing the thickness of a flange formed of materials having a uniform density. In an alternative embodiment, the flange can have a uniform thickness and an increasing porosity as an imaginary point proceeds toward the free edge of the flange. A decreasing stiffness also can be achieved by decreasing thread counts of flanges formed of fabric. The decreasing stiffness can be achieved by decreasing the packing density of fibers in flanges formed of felt-like fibrous materials. The stiffness of the flange also can be controlled by combining some of the foregoing structures, such as for example varying the porosity and tapering the flange, or varying the density of the material as the flange tapers toward the free edge.

The flange preferably supports the dispensing means, whether it be the container or the pieces. The dispensing means can be made an integral part of the flange. The dispensing means is disposed so as to permit the bioreactive agent contained therein to be diffused in the vicinity of the interface between the conduit and the skin through which it leads.

The present invention also includes means for permitting the dispensing means to be refilled with the bioreactive agent. One alternative embodiment of such refilling permitting means preferably includes a portion of the dispensing means capable of penetration by an instrument for introducing the bioreactive agent into the dispensing means and resealing itself after any such penetration by such instrument. For example, an instrument such as a hypodermic needle can be used to penetrate a portion of the container and inject an additional amount of the bioreactive agent into the receptacle of the container. The penetrated portion of the container reseals itself after the needle is withdrawn. Materials suitable for forming a penetrable portion of the container include silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon. Moreover, this same means of refilling the pieces of polymethylmethacrylate also is effective insofar as the hypodermic needle can be inserted into the pieces to inject an additional amount of the bioreactive agent.

In an alternative preferred embodiment of the refilling permitting means, an access opening is provided. The access opening can be sealed by application of a sealant such as wax or other malleable sealant which is removable without contaminating the bioreactive agent to be stored in the receptacle.

In a yet further alternative preferred embodiment of the refilling permitting means, at least one access opening is provided. A channel is provided through the conduit wall so that one end of the channel joins with the access opening, and the other end of the channel terminates in an exit opening defined through the conduit wall. Preferably, the exit opening of the channel joins with a flexible tube, which leads outside the body in which the implant is contained. Preferably, two access openings, two channels, two exit openings, and two flexible tubes are provided so that a bioreactive agent can be circulated into the receptacle and out of the receptacle, if desired. In this way, one bioreactive agent can be flushed out of the receptacle and replaced by another bioreactive agent, which may not be compatible with the predecessor bioreactive agent. It also is possible to seal off one of the exit openings or provide only a single exit opening and a single access opening. In these latter two embodiments, it is possible to supply the bioreactive agent under a positive pressure to increase the rate of diffusion. It also is possible to apply a negative pressure, i.e., a vacuum or suction, to remove the bioreactive agent.

The refilling permitting means of the present invention allows a necessary degree of control over the local concentration of bioreactive agent.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1 is a perspective view of a schematic representation of a preferred embodiment of the present invention;

FIG. 2 is a cross-section of the device of FIG. 1;

FIG. 3 is a cross-sectional view of a schematic representation illustrating an alternative preferred embodiment of the present invention;

FIG. 4 is a cross-sectional view of a schematic representation diagram illustrating an alternative preferred embodiment of the present invention;

FIG. 5 is a cut-away prospective view of a schematic representation illustrating an alternative preferred embodiment of the present invention;

FIG. 6 is a cross-sectional view of a schematic representation illustrating an alternative preferred embodiment of the present invention;

FIG. 7 is a partial cross-sectional view of a schematic representation illustrating an alternative preferred embodiment of the present invention;

FIG. 8 is a cross-sectional view of a schematic representation illustrating an alternative preferred embodiment of the present invention;

FIG. 9 is a perspective view of a schematic representation of an alternative preferred embodiment of the present invention;

FIG. 10 is a cross-section taken along the line of sight designated 10—10 of the device of FIG. 9; and FIG. 11 is a cross-sectional view of an alternative embodiment of the present invention.

DETAILED DESCRIPTION OF THE PREFERRED EMBODIMENTS

Reference now will be made in detail to the present preferred embodiments of the present invention, examples of which are illustrated in the accompanying drawings.

A preferred embodiment of the pharmaceutically protected percutaneous implant device of the present invention is shown in FIG. 1 for example and is represented generally by the numeral 20.

The percutaneous device of the present invention includes a conduit for leading through the skin of a living human being or animal. As embodied herein and shown for example in FIGS. 2, 3, 4, 6, 8, and 10, a conduit 24 extends through an opening through skin 28 in a living human being or animal. Conduit 24 comprises a tube or pipe that also passes through the body's subcutaneous tissue 32. Conduit 24 preferably is formed of a bio-compatible material such as silicon, titanium, polycarbonate, etc. Preferably, only the tissue interfacing surface of the conduit need be formed of a bio-compatible material. Accordingly, various composite structures are suitable as conduits for purposes of the present invention.

In accordance with the present invention, means are provided for dispensing a bioreactive agent during the useful life of the percutaneous device. The dispensing means preferably contacts the conduit and at least partly surrounds the conduit. Preferably, the dispensing means is disposed on the portion of the conduit contacting the subcutaneous tissue and near where the conduit passes through the skin. The dispensing means is located so as to be able to dispense the bioreactive agent into the subcutaneous tissue in the vicinity where the conduit passes through the skin. Moveover, the dispensing means preferably is structured so as to maintain a predetermined size and so does not diminish while continuously dispensing the bioreactive agent during the useful life of the percutaneous device. This avoids the production of voids in the subcutaneous tissue.

In one preferred embodiment shown in FIGS. 1, 2, 3, 9, 10, and 11 for example, the means for dispensing a bioreactive agent includes a container 36 having a hollowed receptacle 40 for storing a bioreactive agent 44. Container 36 at least partly surrounds conduit 24 and preferably completely surrounds conduit 24. Container 36 preferably is disposed beneath the skin and in the subcutaneous tissue so as to permit the bioreactive agent to be diffused into the subcutaneous tissue in the vicinity of the interface between conduit 24 and the skin through which conduit 24 leads.

Container 36 preferably is formed of one or more of the following materials: silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon.

Container 36 preferably includes a tissue interfacing wall 48 which is permeable to the bioreactive agent in order to permit the bioreactive agent to be diffused through wall 48 and into the body tissue adjacent wall 48.

Moreover, tissue interfacing wall 48 preferably is formed of a material having a permeability co-efficient which is temperature dependent, and preferably this temperature dependence is such that the permeability of wall 48 increases as the temperature increases. Examples of materials suitable for forming the tissue interfacing wall having a temperature dependent diffusion coefficient include silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon. Such materials can be formed with varying porosities according to known techniques, and these porosities can be controlled to optimize them for a preselected bioreactive agent and a desired diffusion rate.

In another preferred embodiment shown for example in FIGS. 4, 5, 6, 7, and 8, the means for continuously dispensing a bioreactive agent during the active life of the percutaneous device includes a plurality of solid pieces 52 for containing a bioreactive agent in solid solution. The pieces have at least a surface portion 64 forming a free surface for interfacing with the tissue of the body in which the implant is embedded. As shown for example in FIGS. 7 and 8, pieces 52 disposed in a flange 56 have a tissue interfacing surface 64 forming part of the surface of flange 56 which interfaces with the tissue surrounding implant 20. Pieces 52 can be formed of polymethylmethacrylate for example and used to hold a bioreactive agent such as Gentamicin in solid solution to be dispensed by gradual diffusion into the tissue over a period of many years.

Suitable bioreactive agents include antimicrobial agents, growth hormones, anti-inflammatory drugs, broad spectrum antibiotics, and antifungal agents, to name a few. Some specific examples of suitable bioreactive agents include the following antimicrobial agents effective against Gram Positive Bacteria: Penicillin G, Methicillin, Nafcillin, Oxacillin, Rifampin, Vancomycin, Streptomycin, Cephalosporins, and Bacitracin. Some specific examples of suitable bioreactive agents include the following antimicrobic agents effective against Gram Negative Bacteria: Neomycin, Polymyxins, and Vancomycin. Some specific examples of suitable bioreactive agents include the following broad spectrum antimicrobic agents: Gentamicin, Ampicillin, Chloramphenicol, Kanamycin, Sulfa drugs, and Tetracycline. Some specific examples of suitable bioreactive agents include the following anti-inflammatory drugs: Cortisone and steroids. Some specific examples of suitable bioreactive agents include the following antifungal agents: Amphotericin B, Clotrimazole, and Nystatin. Moreover, suitable bioreactive agents can be formed by known effective combinations of any of the foregoing, which also can be provided in different solutions as desired. In addition, different bioreactive agents can be alternated so as to alter the treatment required by the implant during different stages of its useful life.

One of the purposes behind the requirement that the size of container 36 or pieces 52 be maintained during dispensing of the bioreactive agent is the avoidance of voids which might provide sites for the initiation of inflammation or infection. Another purpose is to facilitate location of a suitable site for refilling container 36 or pieces 52 with bioreactive agent as described hereinafter in order to further prolong the useful life of implant 20.

Figure 1:
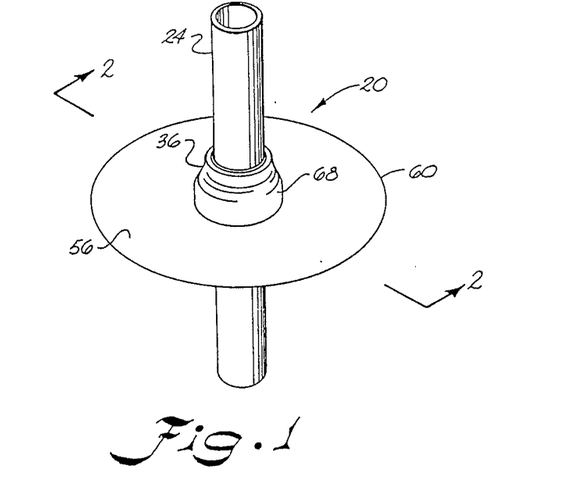
Figure 2:
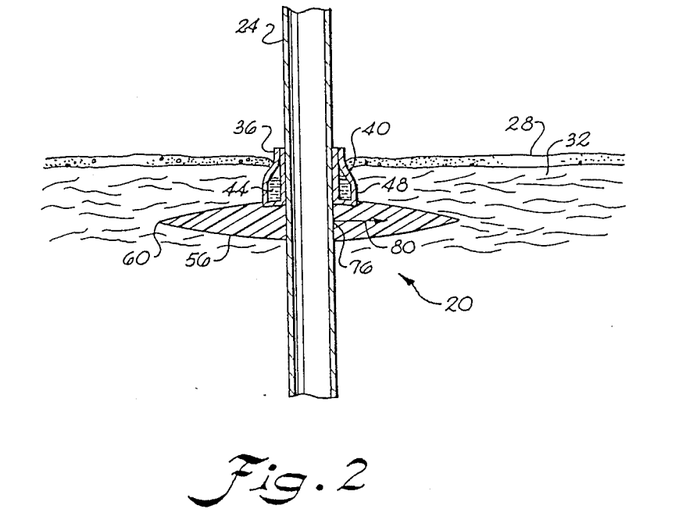
Figure 6:
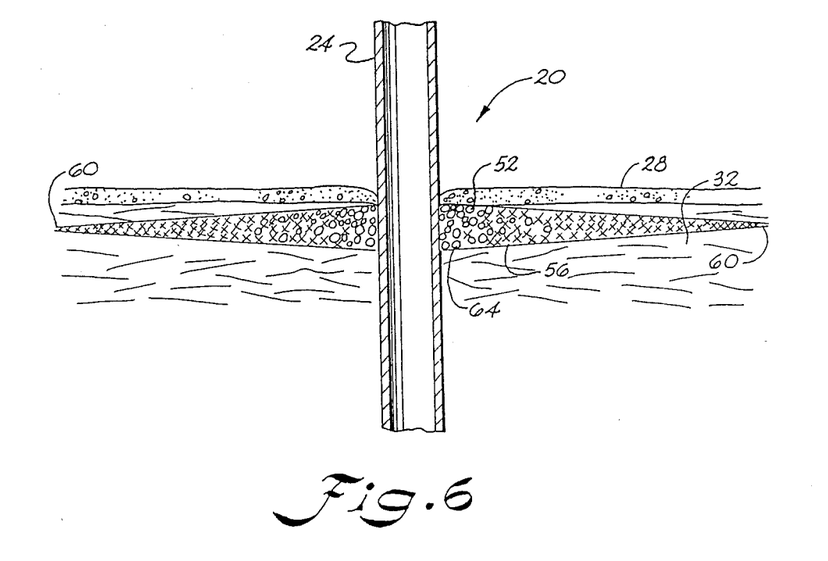
Figure 7:
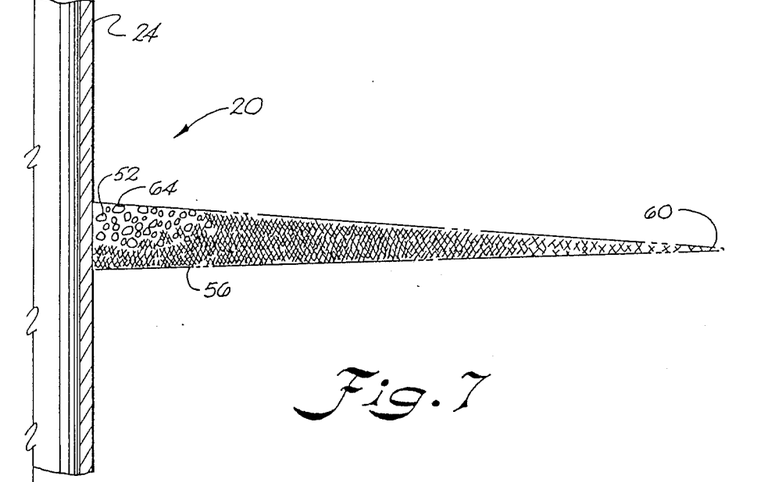
Figure 8:
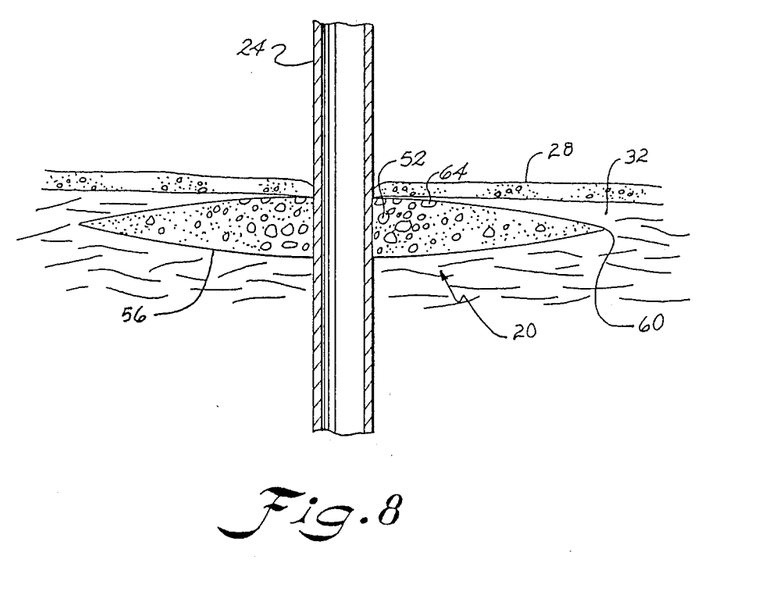

In an alternative preferred embodiment of the present invention, a flange 56 surrounds conduit 24. As shown in FIGS. 1-11, flange 56 extends radially outwardly from conduit 24 to a free edge 60. The stiffness of flange 56 preferably decreases gradually as an imaginary point 76 moves from the portion of flange 56 contacting conduit 24 in the direction of arrow 80 to free edge 60 of flange 56. As shown in FIGS. 2 and 6 for example, The decreasing thickness results in a decreasing stiffness of flanges formed of materials having a uniform density. In an alternative embodiment (not shown), flange 56 can have a uniform thickness and a stiffness which decreases as an imaginary point moves from the portion of flange 56 contacting conduit 24 to free edge 60 by increasing the porosity as the imaginary point proceeds toward free edge 60 of the flange. The decreasing stiffness also can be achieved by decreasing thread counts of flanges formed of fabric such as shown for example in FIGS. 4 and 5. The decreasing stiffness can be achieved by decreasing the packing density of fibers in flanges formed of felt-like fibrous materials such as shown for example in FIG. 7. The stiffness of the flange also can be controlled by combining some of the foregoing structural techniques, such as for example varying the porosity and tapering the flange, or varying the density of the material as the flange tapers toward free edge 60.

Figure 11:
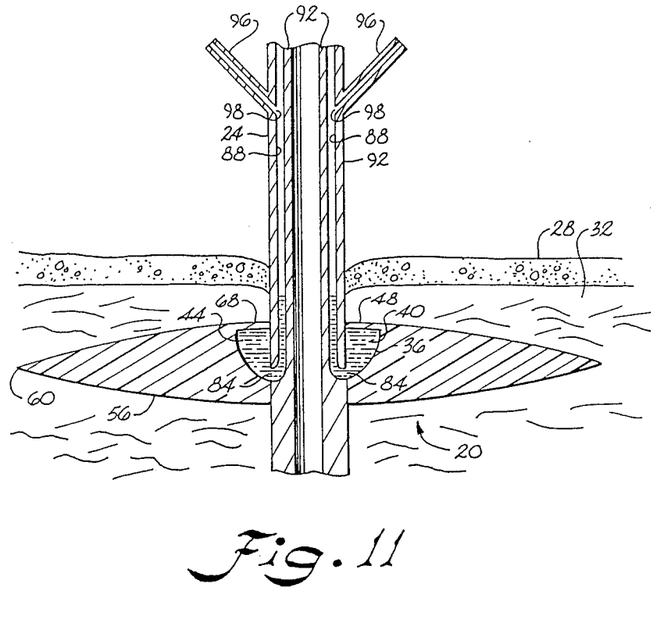

Flange 56 preferably supports the dispensing means, whether it be container 36 or pieces 52. As shown in FIGS. 4-8 for example, pieces 52 are disposed so as to permit the bioreactive agent contained therein to be diffused in the vicinity of the interface between conduit 24 and the skin through which it leads. As shown in FIG. 11 for example, container 36 can be formed integrally with flange 56, and tissue interfacing wall 48 forms an integral part of the surface of flange 56.

In further accordance with the present invention, means are provided for permitting the dispensing means to be refilled with the bioactive agent. One alternative embodiment of such refilling permitting means preferably includes a portion of the dispensing means capable of penetration by an instrument for introducing the bioactive agent into the dispensing means and resealing itself after any such penetration by such instrument. As embodied herein and shown in FIGS. 1 and 11 for example, the refilling permitting means preferably includes a portion 68 of container 36 capable of penetration by an instrument (not shown) for introducing a bioactive agent into container 36 and resealing itself after any such penetration by such instrument. An instrument such as a hypodermic needle can be used to penetrate portion 68 of container 36 and inject an additional amount of the bioactive agent into receptacle 40 of container 36. Upon removal of the needle, portion 68 of container 36 reseals itself after the needle is withdrawn. Materials suitable for forming portion 68 of container 36 include silicone rubber, polytetrafluoroethylene, acrylic copolymers cast on polymeric substrates such as VERSAPOR manufactured by Gelman Sciences of Ann Arbor, Mich., polysulfone, polyurethanes, polyethylene, and nylon. Moreover, this same means of refilling pieces 52 of polymethylmethacrylate also is effective insofar as the hypodermic needle can be inserted into pieces 52 to inject an additional amount of the bioactive agent such as Gentamicin.

Figure 3:
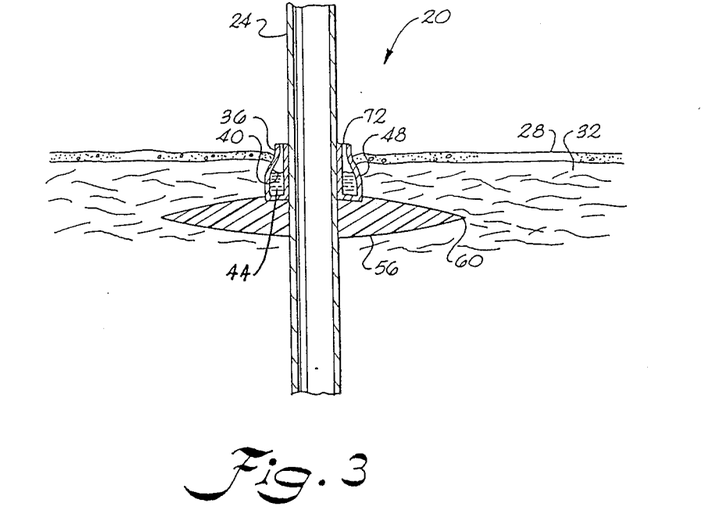
Figure 4:
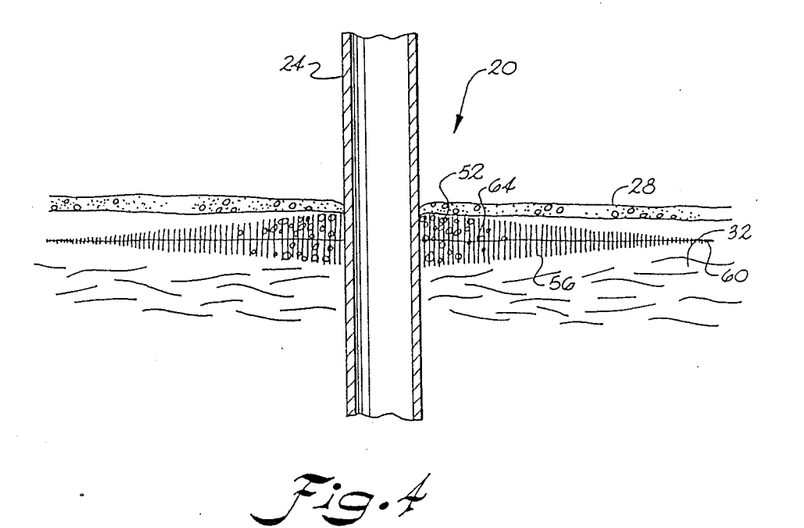
Figure 5:
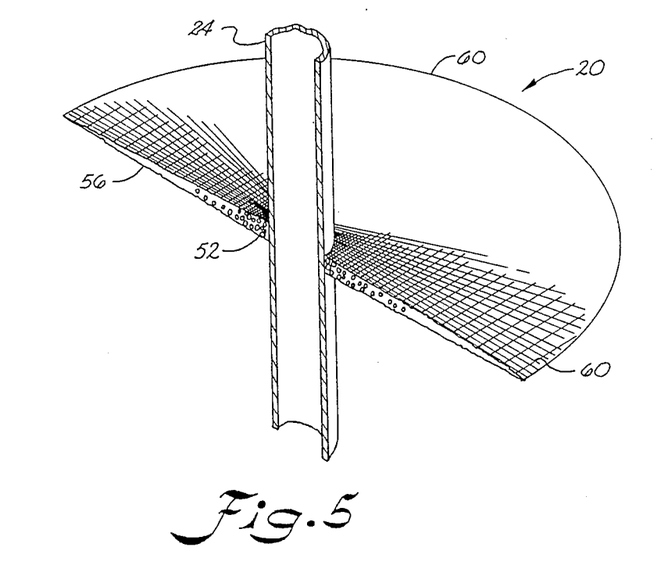

In an alternative preferred embodiment of the refilling permitting means, an access opening 72 is provided as shown for example in FIG. 3. Access opening 72 can be sealed by application of a sealant such as wax or other malleable sealant which is removable without contaminating the bioactive agent to be stored in receptacle 40.

Figure 9:
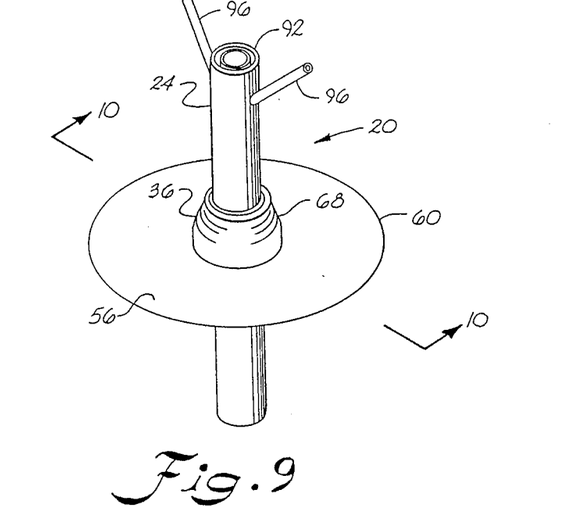
Figure 10:
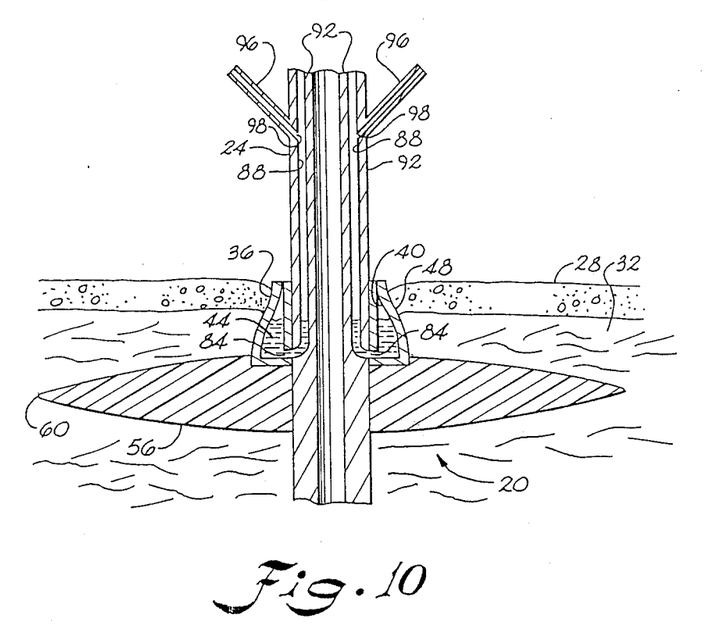

In a yet further alternative preferred embodiment of the refilling permitting means, at least one access opening 84 is provided as shown for example in FIGS. 10 and 11. A channel 88 is provided through conduit wall 92 so that one end of channel 88 joins with access opening 84, and the other end of channel 88 terminates in an exit opening 98 defined through conduit wall 92. Preferably, as shown in FIGS. 9, 10, and 11, exit opening 98 of channel 88 joins with a flexible tube 96, which leads outside the body in which implant 20 is contained. As shown in FIGS. 9, 10, and 11 for example, preferably two access openings 84, two channels 88, two exit openings 98, and two flexible tubes 96 are provided so that a bioactive agent can be circulated into receptacle 40 and out of receptacle 40, if desired. In this way, one bioactive agent can be flushed out of receptacle 40 and replaced by another bioactive agent, which may not be compatible with the predecessor bioactive agent. It also is possible to seal off one of the exit openings or provide only a single exit opening and a single access opening. In these latter two embodiments, it is possible to supply the bioactive agent under a positive pressure to increase the rate of diffusion. However, it sometimes may be desirable to remove the bioactive agent from container 36 in the embodiments shown in FIGS. 9—11 for example. In such cases, it is possible to seal off the opening at the end of one of tubes 96 and apply a negative pressure to the opening of the other tube 96. This will withdraw the bioactive agent from receptacle 40. Having effected this withdrawal, a different bioactive agent, even one incompatible with the first, can be introduced into receptacle 40, either under the force of gravity, capillary action or by application of a positive pressure.

The refilling permitting means of the present invention allows a necessary degree of control over the local concentration of bioactive agent. As is known, the rate of diffusion of a substance through a permeable membrane depends upon the relative concentration of the substance on opposite sides of the membrane. Thus, if the local concentration of the bioactive agent on the outside of tissue interfacing wall 48 should become higher than the concentration inside receptacle 40, then the flow of bioactive agent to the tissue interfacing with tissue interfacing wall 48 ceases or becomes reduced to a point where it becomes ineffective for its intended purpose. On such occasions, or to avoid such occasions, the store of bioactive agent inside container 36 or pieces 52 can be replenished at predetermined intervals. In this way, the useful life of the percutaneous device of the present invention can be extended indefinitely for the full lifetime of the living host.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A percutaneous device for implantation into a living host such as a human being or an animal, comprising:
    (a) a conduit for leading through the skin of the human being or animal into the body of same;
    (b) means for dispensing a bioactive agent during the useful life of the percutaneous device in the living host, said dispensing means contacting said conduit and at least partly surrounding said conduit, said dispensing means having a predetermined size and maintaining said size during dispensing of said agent;
    (c) a flange surrounding said conduit and extending radially outwardly therefrom to a free edge of said flange and having a thickness gradually decreasing as an imaginary point moves through said flange radially outwardly to said free edge of said flange, said flange supporting said dispensing means;
    (d) said dispensing means including means for permitting said dispensing means to be refilled with said bioactive agent while the device remains implanted in the living host, said refilling permitting means including a portion of said dispensing means capable of penetration by an instrument for introducing said agent into said dispensing means and resealing after any such penetration by such instrument;
    (e) said dispensing means having a subcutaneous tissue interfacing surface, said surface being permeable to said bioactive agent to permit said agent to be diffused through said subcutaneous tissue interfacing surface and into the tissue adjacent said surface; and
    (f) said subcutaneous tissue interfacing surface of said dispensing means having a permeability coefficient such that permeability increases with an increase in temperature.

2. A device as in claim 1, further comprising:
    a flange surrounding said conduit and extending radially outwardly therefrom to a free edge of said flange and having a thickness gradually decreasing as an imaginary point moves through said flange radially outwardly to said free edge of said flange, said flange supporting said dispensing means.

3. A device as in claim 2, wherein:
said dispensing means includes a plurality of pieces of polymethylmethacrylate disposed in said flange near said conduit and having at least a portion thereof forming a portion of the free surface of said flange nearest the skin of the human being or animal.

4. A device as in claim 7, wherein:
said bioreactive agent comprises Gentamicin.

5. A percutaneous device for a human being or an animal, comprising:
(a) a conduit for leading through the skin of the human being or animal into the body of same;
(b) a container having a hollowed receptacle for subcutaneously storing a bioreactive agent, said container at least partly surrounding said conduit; and
(c) said container having a subcutaneous tissue interfacing wall, said wall being permeable to said bioreactive agent to permit said agent to be diffused through said subcutaneous tissue interfacing wall and into the subcutaneous tissue adjacent said wall.

6. A device as in claim 5, wherein:
said container is disposed so as to permit said agent to be diffused in the vicinity of the interface between said conduit and the skin through which it leads.

7. A device as in claim 5, further comprising:
means for permitting said container to be refilled with said agent.

8. A device as in claim 7, wherein:
said refilling permitting means includes at least one access opening disposed in said container so as to be accessible from outside the body containing the percutaneous device.

9. A device as in claim 8, wherein:
said conduit includes a wall having at least one channel having one end connected to one of said access openings disposed in said container and having an opposite end terminating in an exit opening defined through said conduit and connected to a tube disposed so as to be accessible from outside the body containing the percutaneous device.

10. A device as in claim 9, wherein:
two said access openings are disposed in said container and two said channels are disposed in said conduit wall, one of said channels having one end connected to one of said access openings and the other of said channels having one end connected to the other of said access openings.

11. A device as in claim 7, wherein:
said refilling permitting means includes a portion of said container capable of penetration by an instrument for introducing a bioreactive agent into said container and resealing after any such penetration by such instrument.

12. A device as in claim 5, wherein:
said tissue interfacing wall of said container has a permeability coefficient which is temperature dependent.

13. A device as in claim 12, wherein:
said permeability coefficient falls within a range such that permeability increases with an increase in temperature.

14. A device as in claim 5, further comprising:
a bioreactive agent disposed within said receptacle, said agent being one of the group of bioreactive agents including antimicrobial agents, growth hormones, anti-flammatory drugs, and antifungal agents.

15. A percutaneous device for a human being or an animal, comprising:
(a) a conduit for leading through the skin of the human being or animal into the body of same;
(b) a container having a receptacle for subcutaneously storing a bioreactive agent, said container at least partly surrounding said conduit;
(c) a bioreactive agent disposed within said receptacle;
(d) said container having a subcutaneous tissue interfacing wall being permeable to said agent to permit said agent to be diffused through said wall into the subcutaneous tissue adjacent said wall, said permeability of said wall increasing with increasing temperature of said wall; and
(e) said container being disposed so as to permit said agent to be diffused subcutaneously in the vicinity of the interface between said conduit and the skin through which it leads.

16. A device as in claim 15, further comprising:
means for permitting said container to be refilled with said agent.

17. A device as in claim 16, wherein:
said refilling permitting means includes an access opening disposed in said container so as to be accessible from outside the body containing the percutaneous device.

18. A device as in claim 16, wherein:
said refilling permitting means includes a portion of said container capable of penetration by an instrument for introducing a bioreactive agent into said container and resealing after any such penetration by such instrument.

19. A percutaneous device for implantation into a living host such as a human being or an animal, comprising:
(a) a conduit for leading through the skin of the human being or animal into the body of same;
(b) a container having a hollowed receptacle for subcutaneously storing a bioreactive agent, said container at least partly surrounding said conduit;
(c) a bioreactive agent disposed within said receptacle;
(d) said receptacle having a subcutaneous tissue interfacing wall being permeable to said agent to permit said agent to be diffused through said tissue interfacing wall into the subcutaneous tissue adjacent said wall;
(e) said receptacle being disposed so as to permit said agent to be diffused subcutaneously in the vicinity of the interface between said conduit and the skin through which it leads; and
(f) means for permitting said receptacle to be refilled with said agent while the device remains implanted in the living host, said refilling permitting means including a portion of said receptacle capable of penetration by an instrument for introducing agent into said receptacle and resealing after any such penetration by such instrument.

20. A device as in claim 19, wherein:
said container completely surrounds said conduit.

* * * * *

UNITED STATES PATENT AND TRADEMARK OFFICE
CERTIFICATE OF CORRECTION

PATENT NO. : 4,959,054

DATED : September 25, 1990

INVENTOR(S) : HEIMKE ET AL

It is certified that error appears in the above-identified patent and that said Letters Patent is hereby corrected as shown below:

Column 11, line 12: change "7" to read --3--.

Column 12, line 47: change "receptable" to read --receptacle--.

Signed and Sealed this

Twenty-fifth Day of February, 1992

Attest:

HARRY F. MANBECK, JR.

Attesting Officer

Commissioner of Patents and Trademarks